United States Patent [19]

Terada et al.

[11] Patent Number: 5,124,261

[45] Date of Patent: Jun. 23, 1992

[54] GENE ENCODING AQUALYSIN I, RECOMBINANT VECTOR CONTAINING THE SAME AND PROCESS OF PRODUCING AQUALYSIN I

[75] Inventors: Ichiro Terada, Yokohama; Takahisa Ohta, Zushi; Hiroshi Matsuzawa, Toshima, all of Japan; Suk-Tae Kwon, Seoul, Rep. of Korea; Yuko Miyata, Tokyo, Japan

[73] Assignee: Japan Tabacco Inc., Tokyo, Japan

[21] Appl. No.: 326,070

[22] Filed: Mar. 20, 1989

[30] Foreign Application Priority Data

Sep. 30, 1988 [JP] Japan ................................. 243981

[51] Int. Cl.⁵ ....................... C12N 9/52; C12N 15/57; C12N 15/70; C12N 1/21
[52] U.S. Cl. ............................... 435/219; 435/252.33; 435/320.1; 536/27; 935/48; 935/60; 935/73
[58] Field of Search ..................... 435/183, 172.3, 212, 435/220; 935/27, 73, 48, 60

[56] References Cited

PUBLICATIONS

Kwon et al., Eur. J. Biochem., 173, 491–497, 1988.
Matsuzawa et al., Eur. J. Biochem., 171, 441–447, 1988.
Matsuzawa et al., Agric. Biol. Chem., 47(1), 25–28, 1983.
Michailis et al., Ann. Rev. Microbiol. 36: 435–65, 1982.
Suggs et al., PNAS 78: 6613–6617, 1981.

Primary Examiner—Richard A. Schwartz
Assistant Examiner—John L. LeGuyader
Attorney, Agent, or Firm—Bacon & Thomas

[57] ABSTRACT

A gene encoding an enzyme aqualysin I is disclosed. The gene of the present invention comprises a region encoding a signal peptide; a pro-region located downstream the signal peptide-encoding region; a region encoding aqualysin I, which is located downstream the pro-region; and a tail region of aqualysin I, which is located downstream the aqualysin I-encoding region. This invention also provides a recombinant vector comprising the gene. Escherichia coli transformed with the recombinant vector and a process of producing aqualysin I utilizing the Escherichia coli.

8 Claims, 7 Drawing Sheets

```
        SacI
        GAGCTC --------- 1 CTACCGCTACCCCTTCCTCCCGGGACAGAGCACCACCCTGGGGCGGTCGTCACCGACGCCCCCTC

AvrII
   67   ACCAAGGCCCAGGCCAGGCCCTGGCCTAGGACGGGATCGCCCGCCCCGCCCCACACCCCCTGGACGGGGACCTGGTCTTCGCCCTGGCCCTGGGGAGGC

187   AGGGGGGTGGACCCCTACCTCCTCCCGGCTCGGGGCCTACGCCGCCGCCCTCGCCGCGGGCCATGCCGGGGCCGTGTTGGGCGAGGGATGTTGGGGGTGCCTCGCATACCGGC

SmaI
  307   AGCTTGTGCGTAAAAATGAAGAATAACTAATAAAAACCCCTTGACACCCGGGCATCCTTAGGGTTAGCTTTGCCCTCGTGAAATCCACAAAGGAGCGTATGAGGAAGACTTATTGGCTG
                                                                                                  MetArgLysThrTyrTrpLeu

427   ATGGCGCTTTTCGCGGTGCTCGTTTTGGGTGGTTGTCAGATGACGCCTCCCGCTCCGATCCAACCCCTACCTTGGCTGAGGCCTTCTGGCCCAAGGAGGCTCCCGTCTATGGCTGATGAC
  -121  MetAlaLeuPheAlaValLeuValLeuGlyGlyCysGlnMetAlaSerArgSerAspProThrLeuAlaGluAlaPheTrpProLysGluAlaProValTyrGlyLeuAspAsp

PstI
  547   CCTGAAGCTATCCCGGGCCGGTACATTGTGCTCTTTAAGAAGGGGAAGGGTCAGTCTCTGCTCCAAGGTGGCATCACAACCCTGCAGGACACCCTGGCTCCTGCAGGGGTAGTGGTGACC
  -81   ProGluAlaIleProGlyArgTyrIleValLeuPheLysLysGlyLysGlyGlnSerLeuLeuGlnGlyGlyIleThrThrLeuGlnAlaArgLeuAlaProGlnGlyValValValThr

647   CAGGGCCTACACGGGGCCCCTCCAGGGATTTGCGGCGGAGATGGCGCCCCAGGCCTTTAGAGGCCTTCATAGAGGGGACAAGGTGGTACGGGCCTGG
  -41   GlnAlaTyrThrGlyAlaLeuGlnGlyPheAlaAlaGluMetAlaProGlnAlaLeuAlaPheArgGlySerProAspValGluPheIleGluAlaAspLysValArgAlaTrp
```

```
1747  TGGCTTAGGGGCCCCGCCGGAACGGACTTTGACCTCTACCTCTGGCGGTGGGACGGCTCCCGTTGGGTGACCGTGGCTAGCTCTACGGGGCCCACCTCGGAGGAAAGTCTCAGCTACAGC
321   TrpLeuArgGlyProAlaGlyThrAspPheAspLeuTyrLeuTrpArgtrpAspGlySerArgTrpValThrValAlaSerThrGlyProThrSerGluSerLeuSerTyrSer 1867  GGAACTGCTGGCTACTACCTCTGGCTCATCTACGGCCTATAGCGGCTCGGGATGTACGAGTTCTGGCTCCAGCGCCCCTAGGCGAAGGAGTTCTTCCTCCCCTGGAAGCGCCTGGGGGA
361   GlyThrAlaGlyTyrTyrLeuTrpLeuIleTyrAlaTyrSerGlyMetTyrGluPheTrpLeuGlnArgPro***

1987  GGTTTTCCCTTTAGCGTCCTGGGAAAGGGCGAGGACCGCTTCCACCTGGAAGACCTGGCCCCCCGGGCACGGTGAGGGCGATCCGGGCGCCCCCACCTGTGGGGCGCACCTCGGGA

2107  GGAGGTCCTCAAAGGAGTTCACCGGACCCCCGGACACCCCGTTCACCTCCAGGATCACGTCGGGGCACGCCCTCGAGGCCCTAAGCCCGCCGGTGGGCGCCCCGGCCGCCACCACCTCCC
         SacI
2227  CCACCAGGACCCCCGGGGGGGAGGGCCCAGCTCCCGGGGCGAGCTC
```

GENE ENCODING AQUALYSIN I, RECOMBINANT VECTOR CONTAINING THE SAME AND PROCESS OF PRODUCING AQUALYSIN I

BACKGROUND OF THE INVENTION

1. Field of the Invention

This invention relates to a gene encoding an enzyme aqualysin I, a recombinant vector comprising the gene and to *Escherichia coli* transformed with the recombinant vector, as well as to a process of producing aqualysin I utilizing the *Escherichia coli* transformant.

2. Description of the Related Art

Proteases are very important enzymes widely used as additives of detergents, catalyst for synthesizing peptides and as essential components of bioreactors. Aqualysin I is a heat-resistant alkalline protease having the optimum pH of about 10, which is produced by the optimum pH of about 10, which is produced by thermophilic bacterium *Thermus aquaticus* YT-1. Aqualysin I is very stable and is highly resistant to surfactants, so that it is used as an additive of detergents and as a component of bioreactors.

Aqualysin I is conventionally produced by separating the same from the supernatant of the culture of *Thermus aquaticus* YT-1. However, since the culturing temperature of *Thermus aquaticus* is as high as 65° C., the culturing cost is high. Further, since the aqualysin I is purified from the supernatant of the culture, it is likely contaminated with an impurity existing in the culture. Still further, the productivity of aqualysin I by *Thermus aquaticus* YT-1 is not very high.

In order to solve the above-mentioned problems, it has been tried to produce aqualysin I employing a genetic engineering procedure by cutting out the aqualysin I gene from the genome of *Thermus aquaticus* YT-1, recombining the aqualysin I gene with a vector for *Escherichia coli* and expressing the aqualysin I gene in the *Escherichia coli*. However, aqualysin I is toxic to *Escherichia coli*, so that if the aqualysin I gene is expressed in an *E. coli* cell, the cell is killed. For this reason, aqualysin I has not yet been produced by genetic engineering processes.

SUMMARY OF THE INVENTION

Accordingly, the object of the present invention is to provide a process of producing aqualysin I utilizing a genetic engineering technique, by which aqualysin I can be produced in a large amount with low cost, and by which the purification of the produced aqualysin I is easy.

Another object of the present invention is to provide a gene, a recombinant vector and *E. coli* transformed with the recombinant vector, which are utilized in the process of the present invention.

The present inventors intensively studied to find that if aqualysin I structural gene further comprising a signal peptide-encoding region and a pro-region upstream the aqualysin I structural gene and a tail region encoding an amino acid sequence which inhibits the activity of aqualysin I is expressed, the aqualysin I produced in the host cell does not damage the host cell because the aqualysin I is in an inactivated form, and by virtue of the signal peptide, the aqualysin I precursor produced in the host cell is secreted into the periplasm. The present inventors further discovered that by heat-treating the host cell having the aqualysin I precursor in the periplasm, the signal peptide-encoding region, the pro-region and the tail regions are cut off and mature aqualysin I in substantially purified form is secreted outside the host cell, to complete the present invention.

That is, the present invention provides a gene which comprises a region encoding a signal peptide; a pro-region located downstream the signal peptide-encoding region; a region encoding aqualysin I, which is located downstream the pro-region; and a tail region of aqualysin I, which is located downstream the aqualysin I-encoding region.

The present invention also provides a recombinant vector comprising the gene of the present invention, which can express the gene encoding aqualysin I in a host cell.

The present invention further provides an *Escherichia coli* which is transformed with the recombinant vector of the present invention.

The present invention still further provides a process of producing aqualysin I comprising the steps of culturing the *Escherichia coli* of the present invention in a culture medium, heat-treating the cultured *Escherichia coli* and recovering aqualysin I from the culture.

By the present invention, the production of aqualysin I by a genetic engineering technique, which hitherto could not be accomplished, was first attained. That is, by the present invention, the mass production of aqualysin I with low cost was first attained. By the process of the present invention, since aqualysin I is secreted in a substantially purified form, the purification procedure is simple and the contamination of impurities is also reduced.

DETAILED DESCRIPTION OF THE PREFERRED EMBODIMENTS

Figure 1A:
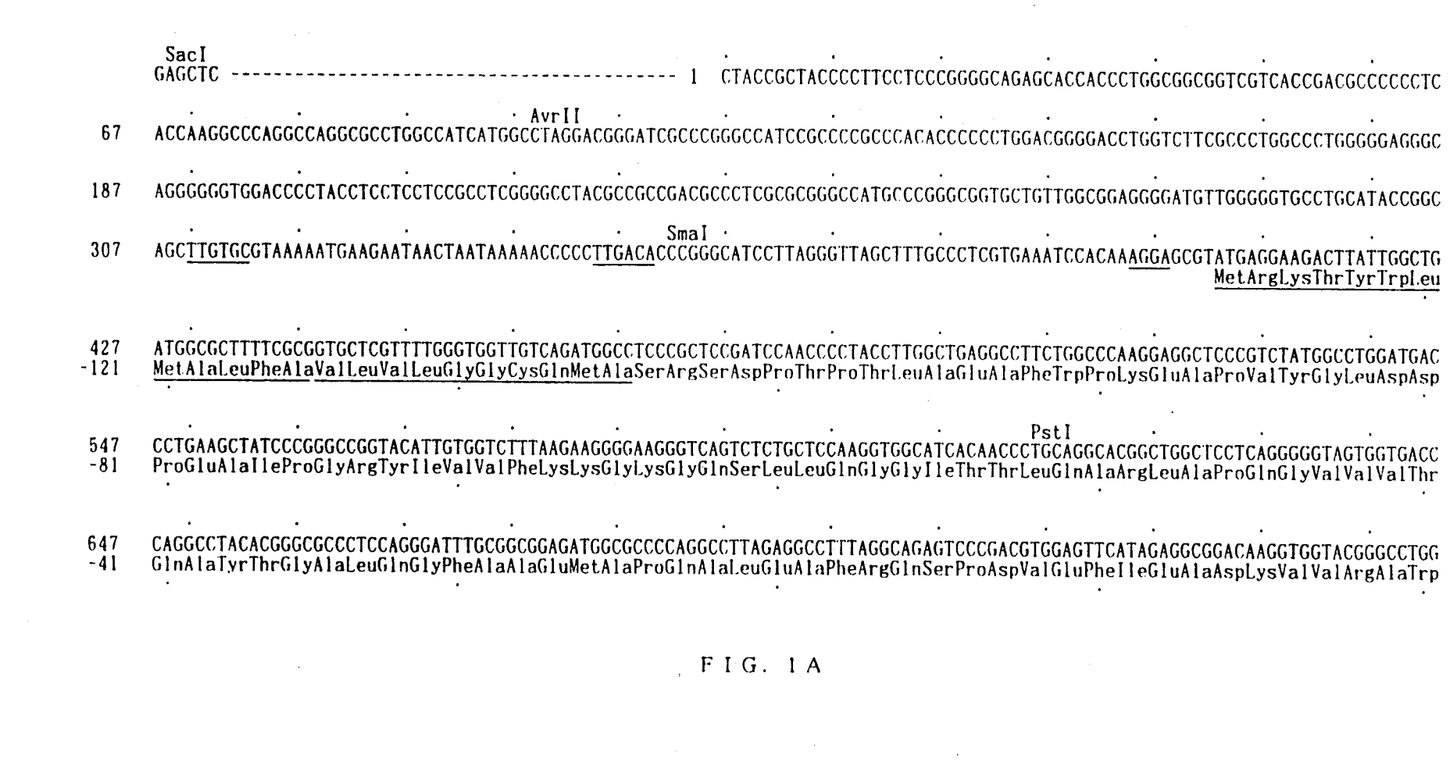
FIG. 1 (parts A–C) shows an example of the base sequence of the aqualysin I precursor gene of the present invention, together with the amino acid sequence encoded by the gene.
Figure 1B:
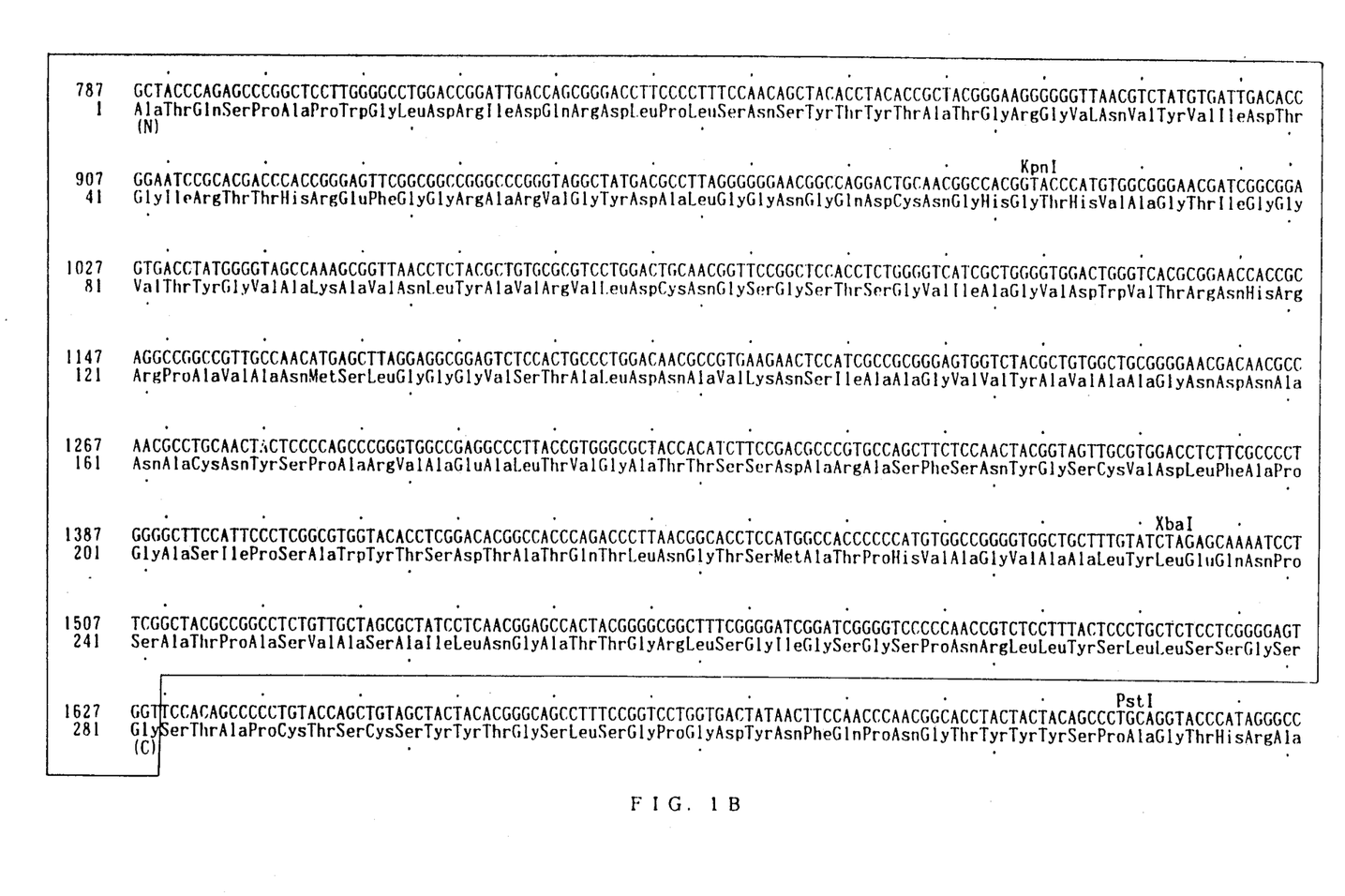
Figure 1C:
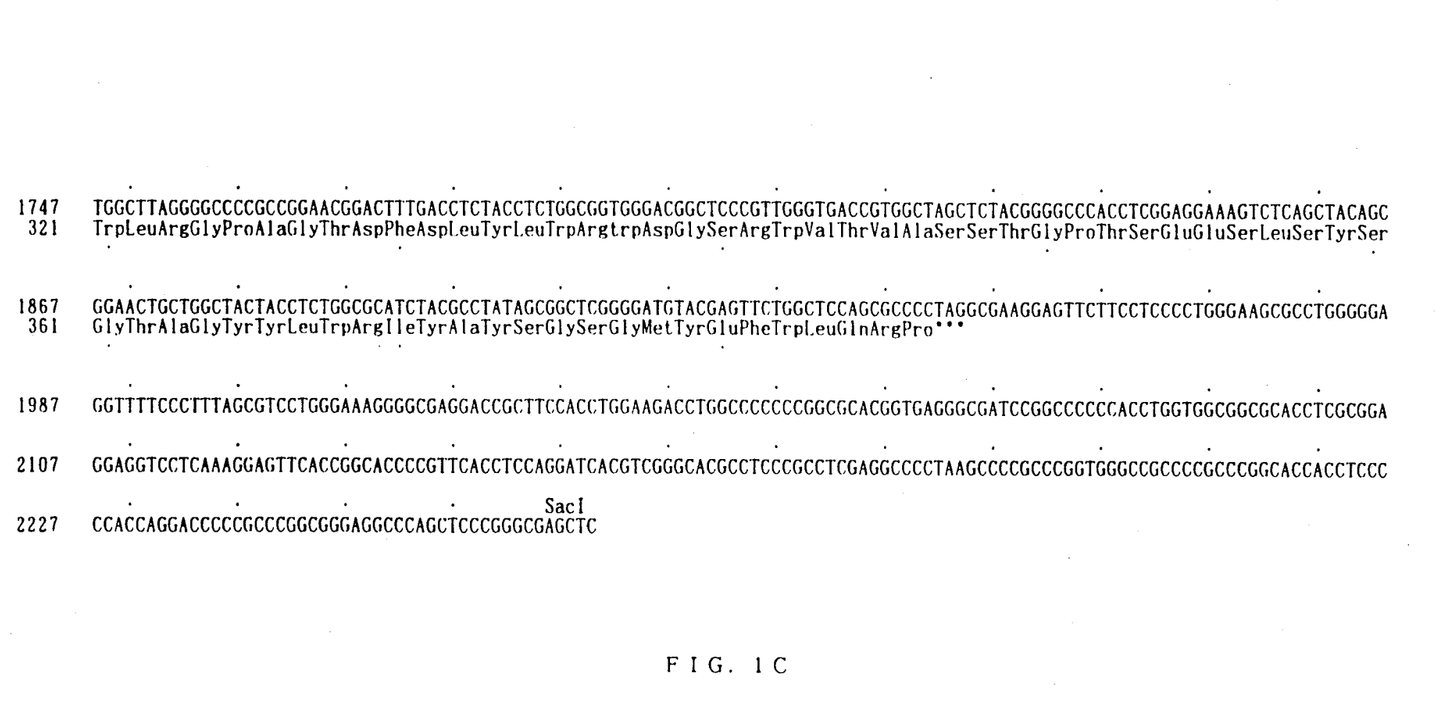

As mentioned above, the gene of the present invention comprises a region encoding a signal peptide (this region is hereinafter referred to as "signal region" for short). In FIG. 1, whole base sequence of a DNA containing the gene of the present invention, which is cloned in the Example hereinbelow described, is shown. In FIG. 1, the signal region is the region from ATG to GCC which is underscored. The signal region shown in FIG. 1 is contained as it is in the DNA of *Thermus aquaticus* YT-1. The signal region has a function to secrete the polypeptide outside the host cell. Some signal regions other than that shown in FIG. 1 are known in the art and are described in, for example, Marison E. et al., "Compilation of Published Signal Sequences", Nucleic Acids Research, vol. 12, No. 13, 1984. In the present invention, any of these known signal regions may be employed. Further, signal regions other than those described in the above-mentioned reference may be employed as long as they have the function to secret the polypeptide outside the host cell.

Downstream the signal region, a region called as pro-region exists. The pro-region is sandwiched between the signal region and the aqualysin I-encoding region hereinafter described (aqualysin I-encoding region is the region encircled by the solid line in FIG. 1). The pro-region concerns the maturation of aqualysin I (cut of the polypeptide at a site between the mature aqualysin I and the pro-region-encoded region). It should be noted that a pro-region other than this pro-region is known in a serine protease (Hiroshi Takagi, "Study about the structure and function of subtilisin of *Bacillus subtilus*", Ph. D thesis of Agricultural Department of The University of Tokyo, 1988), and such a pro-region may also be employed in the present invention.

Downstream the pro-region, a region encoding aqualysin I exists. The aqualysin I-encoding region is contained in the DNA of *Thermus aquaticus* YT-1 and the base sequence thereof is conventionally known (Suk-tae Kwon, "Biochemical and Genetic Engineering Study of Highly Thermophilic Bacterium *Thermus aquaticus* YT-1", Ph. D thesis of Agricultural Department of The University of Tokyo, 1987). In FIG. 1, the aqualysin I-encoding region is encircled by the solid line.

Downstream the aqualysin I-encoding region, a tail region is located. It is believed that the peptide region encoded by the tail region has a function to inactivate aqualysin I, and it also concerns the stabilization of the aqualysin I precursor and the secretion of aqualysin I to the outside of the host cell. By virtue of the tail region, when the aqualysin I precursor gene is expressed in *E. coli*, the aqualysin I is in the inactivated form, so that it does not damage the *E. coli* host. In FIG. 1, the tail region is the region immediately downstream the aqualysin I structural gene to the termination codon TAG (that is, the region for which amino acid sequence is shown, but downstream the aqualysin I-encoding region). The tail region shown in FIG. 1 is naturally occurring in the DNA of *Thermus aquaticus* YT-1. It should be noted, however, any base sequence other than that shown in FIG. 1 may be employed as long as it can inactivate aqualysin I and which does not adversely affect the secretion of aqualysin I.

In general, an amino acid is encoded by one or more codons. Therefore, another base sequence encoding the amino acid sequence shown in FIG. 1 is construed to be the same base sequence as that shown in FIG. 1. Further, it is well recognized by those skilled in the art that a physiological activity of a polypeptide may not be substantially influenced even if a small number of amino acids of the polypeptide are substituted with other amino acids, if a small number of amino acids are deleted from the polypeptide, or if a small number of amino acids are added to the polypeptide. Therefore, even if a small number of bases of one or more of the above-described regions are substituted with other bases or deleted, or small number of bases are added to the base sequence so as to substitute a small number of amino acids of the polypeptide encoded by the region with other amino acids, to delete a small number of amino acids from the polypeptide or to add a small number of amino acids to the polypeptide, if the above-described functions of each region are not substantially influenced, the modified base sequence is construed to be a substantially the same sequence as the base sequence shown in FIG. 1, and so is construed to be within the scope of the present invention. For example, as to the pro-region, if a small number of amino acids of the polypeptide encoded by the pro-region is substituted with other amino acids or deleted from the polypeptide, or if a small number of amino acids are added to the polypeptide, if the functions of the pro-region is exhibited, that is, if the maturation of aqualysin I is accomplished, the modified pro-region is construed to be substantially the same as the pro-region shown in FIG. 1.

The gene of the present invention may include additional DNA sequence in addition to the above-described regions. For example, the gene shown in FIG. 1 additionally includes DNA regions upstream the signal region and downstream the tail region, respectively, and such a gene is encompassed within the scope of the present invention.

The gene of the present invention may be obtained by, for example, cutting out the gene from the genome of *Thermus aquaticus* YT-1 with appropriate restriction enzymes as shown in FIG. 1 and by cloning the cut out gene.

The present invention also provides a recombinant vector which contains the above-described gene of the present invention and which can express the gene in a host cell. The recombinant vector of the present invention contains, similar to the other well-known conventional vectors, a replication origin for replicating the vector in the host cell, a promoter such as tac promoter which is located upstream the gene of the present invention and a terminator such as rrnB $T_1T_2$ which is located downstream the gene of the present invention, and may preferably further contain an appropriate marker such as antibiotics resistance, as well as a repressor such as lac $I^q$. Vectors containing these regions are commercially available and the regions contained in the commercially available vectors may be employed as they are.

The recombinant vector of the present invention may be prepared, for example, by the process hereinbelow described. It should be noted that the recombinant vector of the present invention may be prepared by various processes and the process is not restricted to that described hereinbelow. For example, although in the process hereinbelow described, the gene of the present invention is separated into two fragments at Xba I site in the aqualysin I-encoding region and the separated fragments are re-ligated together after separately cloning the each fragment, the recombinant vector may be prepared without separating the gene into two fragments.

(1) SOURCE OF GENE

The genome of *Thermus aquaticus* YT-1 (ATCC25104) can be utilized as the source of the gene of the present invention.

(2) PREPARATION OF THE GENE OF THE PRESENT INVENTION

The genome DNA of *Thermus aquaticus* YT-1 is completely digested with restriction enzymes Xba I and Sac I, and a DNA fragment (2.8 kbp) encoding the N-terminal region of the aqualysin I and a DNA fragment (0.8 kbp) encoding the C-terminal region of aqualysin I are separately cloned with commercially available vector plasmid pUC12. The DNA fragment encoding the N-terminal region of aqualysin I is partially digested with restriction enzyme Sma I to cut off the 5'-end region which is thought to have promoter activity to obtain a DNA fragment with a size of 1.1 kbp. The unnecessary 3'-end region of the DNA encoding the C-terminal region of aqualysin I is shaved off by a length of 0.1 kbp, and the resultant is ligated with the above-mentioned DNA fragment with a size of 1.1 kb with proper orientation to construct the aqualysin I precursor gene shown in FIG. 1.

(3) VECTOR PLASMID

The plasmid pKK223-3 commercially available from Pharmacia is an expression vector having ampicillin-resistant gene as a selection marker, strong tac promoter upstream the cloning site and a terminator downstream the cloning site. The plasmid pKK223-3 has a replication origin originated from pBR322 and the number of copies is not so large. Therefore, in order to increase the number of copies, the replication origin is preferably exchanged with that of the vector plasmid pUC18 commercially available from Takara Shuzo Co., Ltd. To control the expression of the tac promoter, the lac repressor gene cut out from lac I$^q$ cartridge vector pMJR1560 commercially available from Amersham International PLC is recombined. It is preferred to cut off the unnecessary regions of the resulting expression vector.

(4) CONSTRUCTION OF THE RECOMBINANT VECTOR OF THE PRESENT INVENTION

The aqualysin I precursor gene prepared as mentioned above is inserted in the cloning site of the expression vector pKI223-3 prepared as mentioned above in the proper orientation to obtain the recombinant vector of the present invention.

As mentioned above, the present invention also provides E. coli transformed with the recombinant vector of the present invention. The transformation of E. coli can be conducted by the conventional methods well-known in the art. For example, the transformation may be accomplished by the rubidium method and the transformant may be selected utilizing the selection marker such as antibiotics resistance contained in the recombinant vector.

The present invention further provides a process of producing aqualysin I comprising the steps of culturing the E. coli transformed with the recombinant vector of the present invention, heat-treating the E. coli and recovering aqualysin I from the culture. The culturing of the transformant may be accomplished by the conventional method in an appropriate conventional culture medium containing assimilable carbon and nitrogen, as well as other inorganic nutrients. In cases where the recombinant vector has tac promoter and lac I$^q$ repressor, after growing the E. coli to an appropriate density, the expression of the gene of the present invention may be induced with about 0.2 mM of IPTG under the presence of an antibiotics for selection such as ampicillin. As the basal medium used for the induction, modified H medium (2 wt % of bactotryptone and 0.8% of NaCl) may be employed. The culture may be conducted at 37° C. for several hours. By this, aqualysin I precursor is produced in the host cells and is accumulated in the periplasms.

The heat-treatment of the host cells may be performed by collecting the cells cultured in the induction conditions by centrifugation, and by suspending the cells in a buffer with a temperature of preferably 40°-90° C., more preferably about 65° C. and with a pH of preferably 4-10, more preferably about 7.5. The duration of the heat-treatment may be, for example, several hours. By this heat-treatment, the mature aqualysin I is secreted from the E. coli cells. In this heat-treatment, for the stabilization of aqualysin I, it is preferred to add $CaCl_2$ to the above-mentioned buffer in the amount of preferably about 1-100 mM, more preferably about 10 mM.

The secreted aqualysin I may be recovered and purified by a relatively simple procedure because the aqualysin I is secreted in a considerably purified form. The secreted aqualysin I may be recovered and purified by, for example, centrifuging the cell suspension after the heat-treatment, treating the resulting supernatant with 90% ammonium sulfate, collecting the resulting precipitate, dialyzing the precipitate against a buffer (preferably with a pH of 4-10, more preferably about 6), subjecting the resultant to cation exchange chromatography equilibrated with the same buffer, eluting the sample with 0-0.3 mM NaCl gradient, and by collecting the fractions with activity eluted near 0.06 mM NaCl. The aqualysin I purified by this method was confirmed to exhibit a single band in SDS-polyacrylamide gel electrophoresis.

EXAMPLES

The present invention will now be described by way of an example thereof. It should be noted that the example is presented for the illustration purpose only and should not be interpreted in any restrictive way.

The each procedure hereinbelow described was conducted, unless otherwise specified, in accordance with the procedures described in T. Maniatis et al., "Molecular Cloning. A Laboratory Manual", (1982), Cold Spring Harbor. The restriction enzymes used were those commercially available and they were used in accordance with the instructions of the commercial product.

CONSTRUCTION OF RECOMBINANT VECTOR pAQ1 EXPRESSING AQUALYSIN I PRECURSOR

Chromosomal DNA of *Thermus aquaticus* YT-1 (ATCC25104) was prepared in accordance with the Marmur's method (Marmur, J. (1961) *J. Mol. Biol.*, 3, 208-218). The DNA was completely digested with restriction enzymes Xba I and Sac I to separate the same into a DNA fragment (2.8 kbp, hereinafter referred to as "N-terminal fragment" for short) containing the signal region (S), pro-region (P) and a part of the aqualysin I-encoding region, which encodes the N-terminal side of aqualysin I, and a DNA fragment (0.8 kbp, hereinafter referred to as "C-terminal fragment" for short) containing a part of the aqualysin I-encoding region, which encodes the C-terminal side of the aqualysin I, and the tail region (T). The DNA fragments were separately cloned by recombining them with a commercially available plasmid vector pUC12 (commercially available from Takara Shuzo, Co., Ltd., Kyoto, Japan) (In FIG. 2, step (1)).

On the other hands, commercially available vector pUC18 was digested with Eco RI and Bam HI and the digested mass was treated with Klenow large fragment (hereinafter referred to as "LF" for short), followed by ligation to eliminate the Sma I site to obtain a plasmid vector pUC18 Δ (step (3) in FIG. 2).

The thus obtained pUC18 Δ was digested with Xba I. On the other hand, a plasmid pSXL which is pUC12 containing the N-terminal fragment previously obtained was digested with Avr II and Xba I to shorten the same. These were ligated to obtain a plasmid pAXL (step (2) in FIG. 2).

The pAXL was cut with Sal I and the resultant was subjected to LF treatment. The resultant was partially digested with Sma I and then ligated to obtain a plasmid pBXL (step (4) in FIG. 2).

The pBXL was digested with Xba I and Hind III. On the other hand, plasmid a pXSS which is pUC12 containing the previously prepared C-terminal fragment was digested with Xba I and Hind III. These were ligated to obtain a plasmid pCX (step 5 in FIG. 2). In the pCX, the N-terminal fragment and the C-terminal fragment were ligated, so that a region encoding the complete aqualysin I precursor was inserted therein.

Figure 2A:
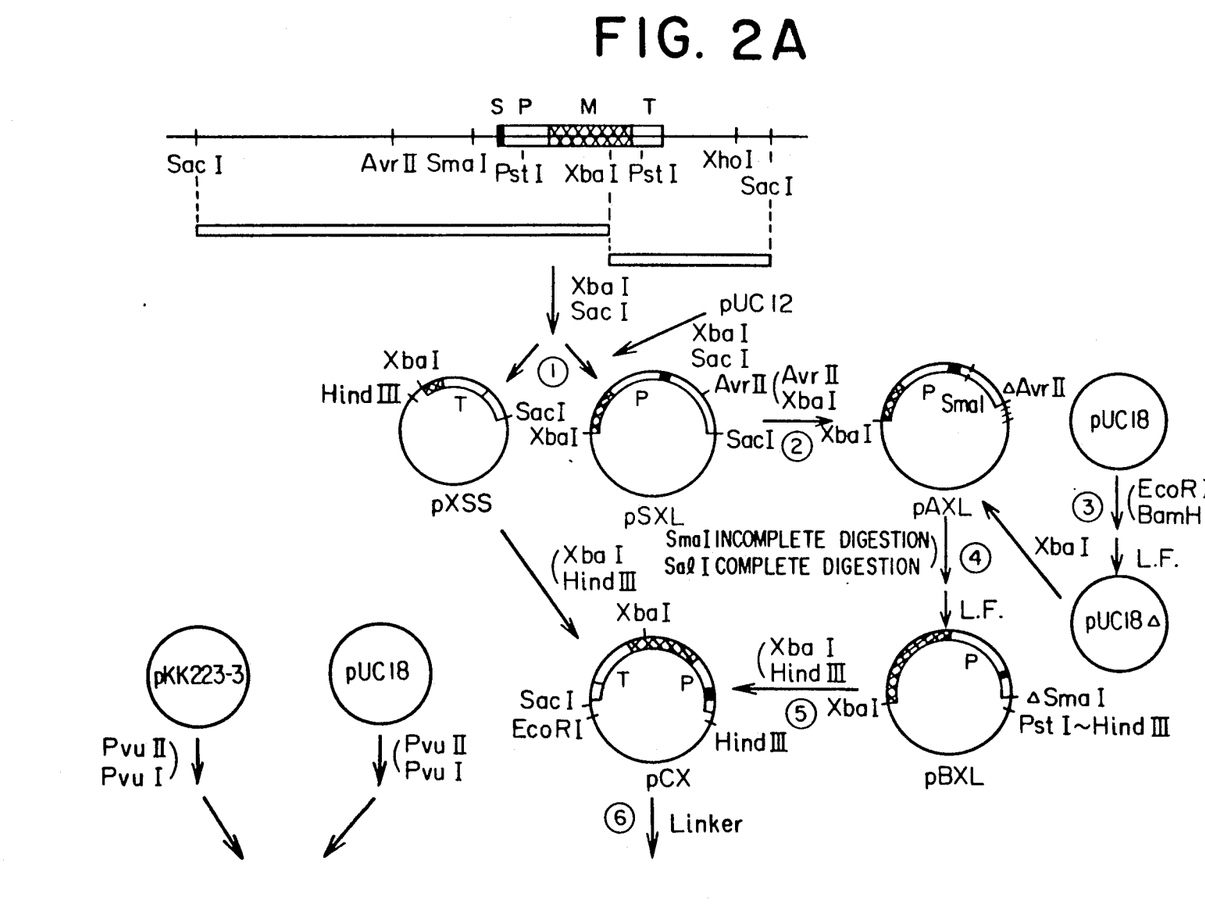
FIG. 2 (parts A–B) shows an example of the steps for constructing an example of the recombinant vector of the present invention, which expresses the aqualysin I precursor of the present invention.
Figure 2B:
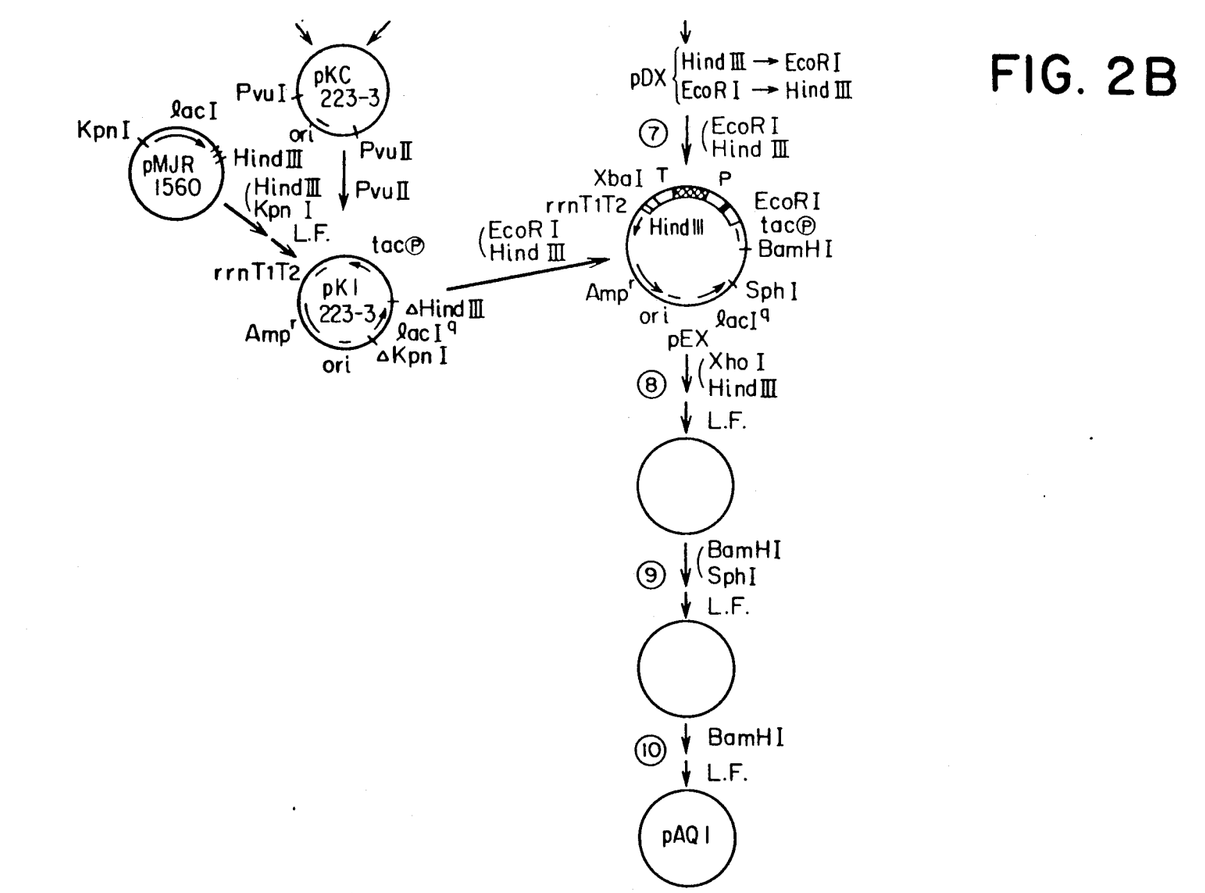
Figure 3:
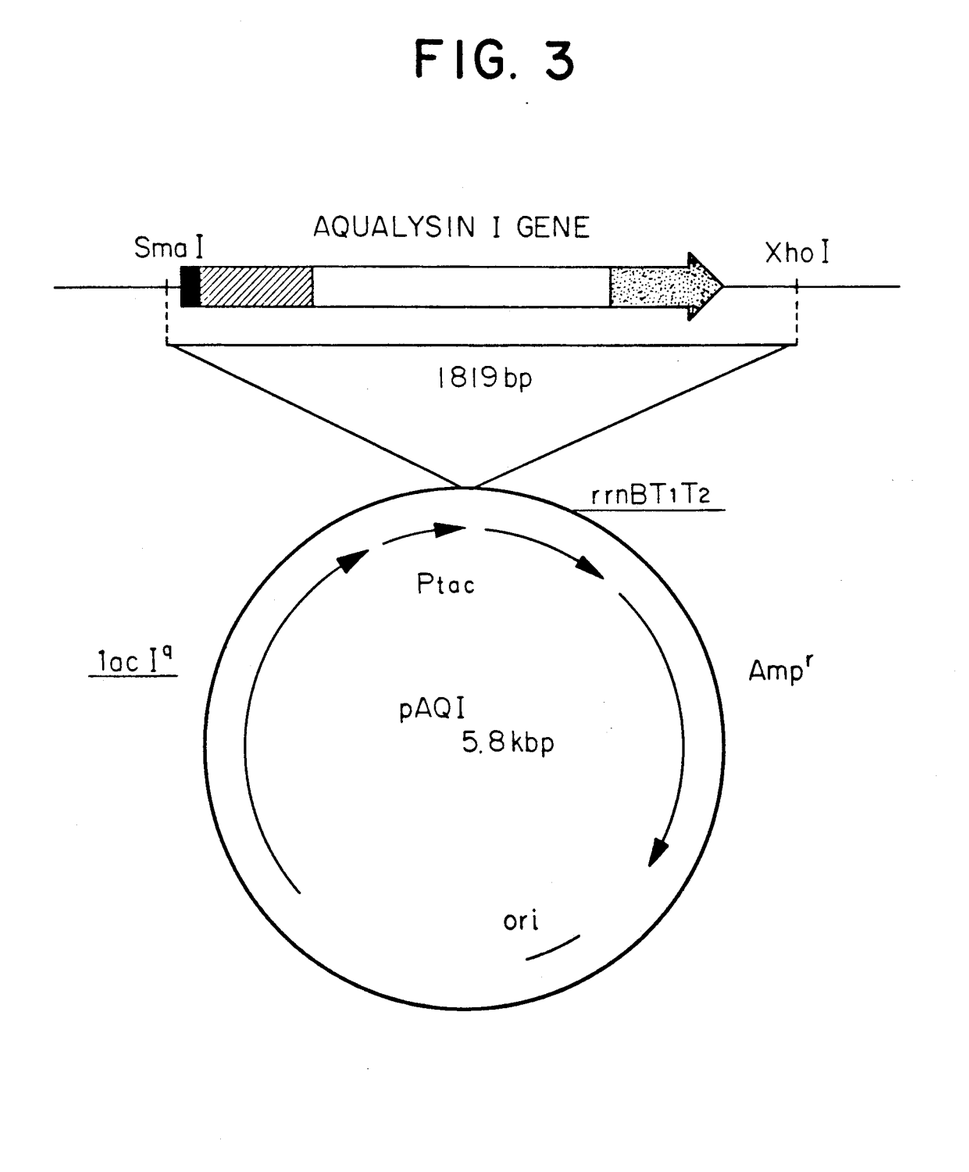
FIG. 3 shows a genetic map of an example of the recombinant vector of the present invention.

Using a linker, the Hind III site in the N-terminal fragment in pCX was changed to Eco RI site, and the Eco RI site in the C-terminal fragment was changed to Hind III site to obtain a plasmid pDX (step (6) in FIG. 2).

A plasmid vector pKK223-3 commercially available from Pharmacia was digested with Pvu II and Pvu I. On the other hand, pUC18 was also digested with these restriction enzymes, followed by ligation of these to obtain a plasmid pKC223-3 in which the replication origin of pKK223-3 was exchanged to that originated from pUC18. The pKC223-3 was digested with Pvu II. On the other hand, lacIq cartridge vector, pMJR1560 was digested with Hind III and Kpn I and the digested mass was subjected to LF treatment. These were ligated to obtain a plasmid vector pKI223-3 which is pKC223-3 containing lacIq gene inserted therein.

The thus obtained pKI223-3 was digested with Eco RI and Hind III. On the other hand, the pDX was digested with the same restriction enzymes. These were ligated to obtain a plasmid pEX which is pKI223-3 containing the aqualysin I precursor gene inserted in the cloning site of pKI223-3 (step (7) in FIG. 2).

The pEX was digested with Xho I and Hind III and the resultant was subjected to LF treatment, followed by ligation to cut off the region of the C-terminal fragment between the Xho I site and the Hind III site (step (8) in FIG. 2). Then the thus obtained plasmid was digested with Bam HI and Sph I and the digested mass was subjected to LF treatment, followed by ligation to cut off the region between the tac promoter and lacIq gene (step (9) in FIG. 2). The resultant was digested with Bam HI and the digested mass was subjected to LF treatment, followed by ligation to eliminate the BamHI site to obtain the desired plasmid pAQI (step (10) in FIG. 2).

Transformation of E. coli With Recombinant Plasmid pAQI

E. coli MV1184 (commercially available from Takara Shuzo, Co., Ltd.) as a host was transformed with the pAQI obtained above by rubidium method well-known in the art, and the transformants were selected based on the resistance to ampicillin to obtain a transformant. The E. coli transformed with pAQI (E. coli MV1184 (pAQI)) was deposited with Fermentation Research Institute, Japan, under an accession number of FERM BP-2305 (the identification of the microorganism is Escherichia coli JTS 873-L2 for clerical reason).

Culturing of E. coli Transformants

Two hundred milliliters of LB medium prepared by adding 100 μg/ml of ampicillin containing 0.1% by weight of glucose was placed in a 500 ml Sakaguchi's flask and 2 ml (1% by volume) of a culture of the E. coli transformants preliminarily cultured in the same culture medium at 30° C. overnight was inoculated thereto. The transformants were cultured at 37° C. for several hours under shaking. After collecting the cells by centrifugation, the cells were suspended in modified H medium (2% by weight of bactotryptone and 0.8% by weight of NaCl) containing 100 μg/ml of ampicillin, and were cultured for another 3 hours to induce the expression of the aqualysin I precursor gene to produce the aqualysin I precursor.

PRODUCTION OF MATURE AQUALYSIN I

Figure 4:
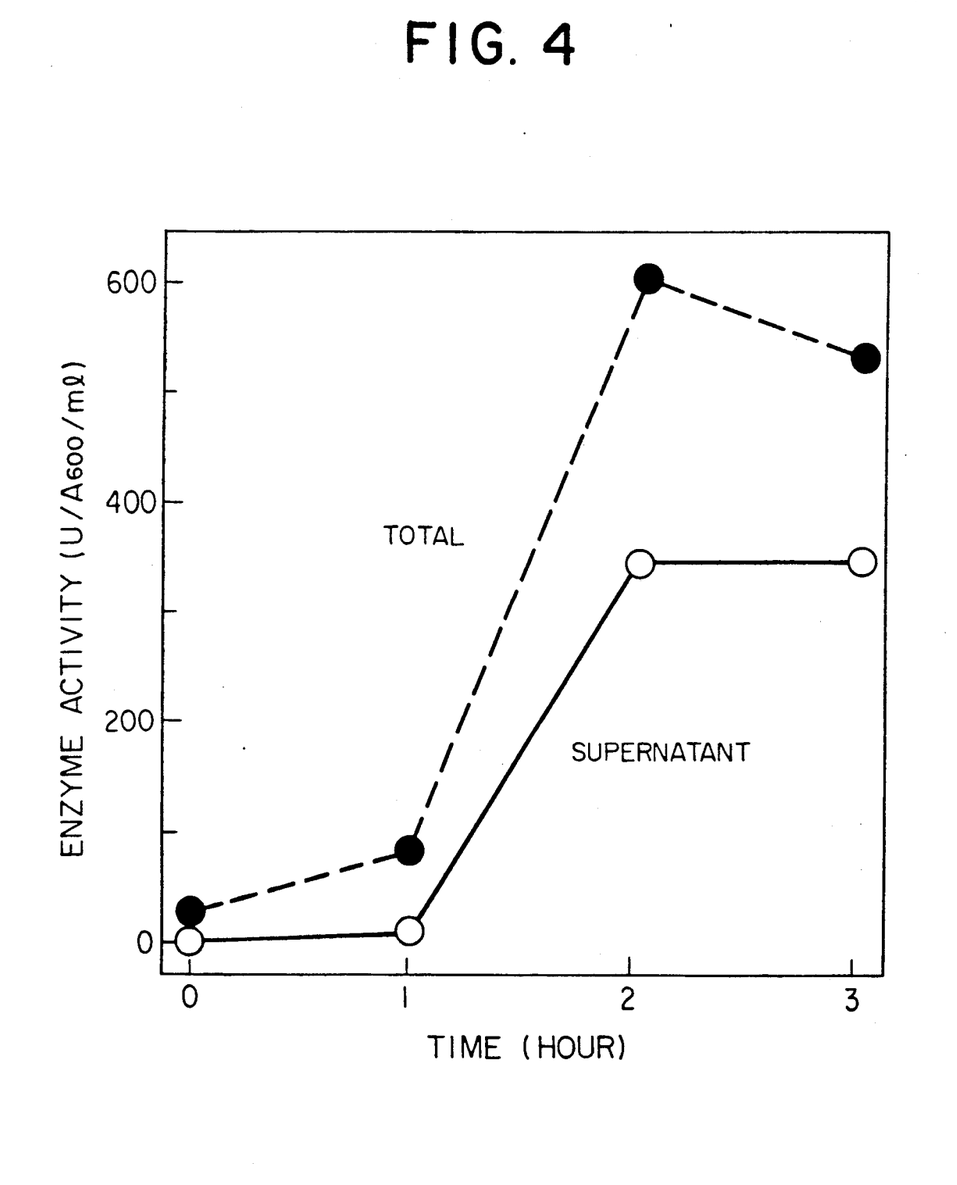
FIG. 4 shows the amount of aqualysin I produced by the process of the present invention with respect to time.

The cells which produced the aqualysin I precursor were collected by centrifugation and the collected cells were suspended in 50 mM HEPES-NaOH buffer containing 10 mM CaCl₂. The suspension was heat-treated at 65° C. for 3 hours. By this, mature aqualysin I was liberated in the buffer with time. The profile of the production of the mature aqualysin I is shown in FIG. 4. In FIG. 4, time is taken along the abscissa and the enzyme activity in terms of casein-decomposing activity (1 unit is the amount of the enzyme which increases the absorbance at 280 nm at a rate of 0.002/min, see Japanese Patent Disclosure (Kokai) No. 152482/83)) was taken along the ordinate. From FIG. 4, it can be seen that mature aqualysin I is secreted by heat-treating the cell.

PURIFICATION OF AQUALYSIN I

After the heat-treatment, the suspension of the cells was centrifuged and ammonium sulfate was added to the supernatant. The precipitate at 90% saturation was collected and was dissolved in the same buffer as the medium of the suspension. The resulting solution was dialyzed against 10 mM phosphate buffer (pH 6.0) containing 1 mM CaCl₂. The resultant was subjected to a cation exchange column equilibrated with the same buffer and was eluted with 0-0.3 mM NaCl gradient. The active fraction was eluted at near 0.06 mM NaCl. The aqualysin I thus purified exhibited a single band in SDS-polyacrylamide gel electrophoresis. The aqualysin I thus obtained was identical with the aqualysin I produced by Thermus aquaticus YT-1 in the electrophoretic behavior and in the immunological properties. The fact that the thus obtained aqualysin I has the same immunogical properties as the aqualysin I produced by Thermus aquaticus YT-1 was confirmed by the Western blotting method described in Cell Technology, vol. 12, No. 8, 1983, p. 1062.

We claim:
1. A cloned gene comprising:
a region encoding a signal peptide;
a pro-region located downstream the signal peptide-encoding region, which encodes the amino acid sequence of:

SerArgSerAspProThrProThrLeuAla

GluAlaPheTrpProLysGluAlaPro

ValTyrGlyLeuAspAspProGluAlaIle

ProGlyArgTyrIleValValPheLys

LysGlyLysGlyGlnSerLeuLeuGlnGly

GlyIleThrThrLeuGlnAlaArgLeu

-continued

AlaProGlnGlyValValValThrGlnAla

TyrThrGlyAlaLeuGlyGlyPheAla

AlaGluMetAlaProGlnAlaLeuGluAla

PheArgGlnSerProAspValGluPhe

IleGluAlaAspLysValValArgAlaTrp.

a region encoding aqualysin I, which is located downstream the pro-region and which encodes the amino acid sequence of:

AlaThrGlnSerProAlaProTrpGlyLeu

AspArgIleAspGlnArgAspLeuPro

LeuSerAsnSerTyrThrTyrThrAlaThr

GlyArgGlyValAsnValTyrValIle

AspThrGlyIleArgThrThrHisArgGlu

PheGlyGlyArgAlaArgValGlyTyr

AspAlaLeuGlyGlyAsnGlyGlnAspCys

AsnGlyHisGlyThrHisValAlaGly

ThrIleGlyGlyValThrTyrGlyValAla

LysAlaValAsnLeuTyrAlaValArg

ValLeuAspCysAsnGlySerGlySerThr

SerGlyValIleAlaGlyValAspTrp

ValThrArgAsnHisArgArgProAlaVal

AlaAsnMetSerLeuGlyGlyGlyVal

SerThrAlaLeuAspAsnAlaValLysAsn

SerIleAlaAlaGlyValValTyrAla

ValAlaAlaGlyAsnAspAsnAlaAsnAla

CysAsnTyrSerProAlaArgValAla

GluAlaLeuThrValGlyAlaThrThrSer

SerAspAlaArgAlaSerPheSerAsn

TyrGlySerCysValAspLeuPheAlaPro

GlyAlaSerIleProSerAlaTrpTyr

ThrSerAspThrAlaThrGlnThrLeuAsn

GlyThrSerMetAlaThrProHisVal

-continued

AlaGlyValAlaAlaLeuTyrLeuGluGln

AsnProSerAlaThrProAlaSerVal

AlaSerAlaIleLeuAsnGlyAlaThrThr

GlyArgLeuSerGlyIleGlySerGly

SerProAsnArgLeuLeuTyrSerLeuLeuSerSerGlySerGly;

a tail region of aqualysin I, which is located downstream the aqualysin I-encoding region and which encodes the amino acid sequence of:

SerThrAlaProCysThrSerCysSerTyr

TyrThrGlySerLeuSerGlyProGly

AspTyrAsnPheGlnProAsnGlyThrTyr

TyrTyrSerProAlaGlyThrHisArg

AlaTrpLeuArgGlyProAlaGlyThrAsp

PheAspLeuTyrLeuTrpArgTrpAsp

GlySerArgTrpValThrValAlaSerSer

ThrGlyProThrSerGluGluSerLeu

SerTyrSerGlyThrAlaGlyTyrTyrLeu

TrpArgIleTyrAlaTyrSerGlySer

GlyMetTyrGluPheTrpLeuGlnArgPro.

2. The gene of claim 1, which encodes the amino acid sequence shown in FIG. 1.

3. The gene of claim 2, which has a base sequence of from base No. 407 to base No. 1948.

4. A recombinant vector comprising the gene of claim 1, which is capable of expressing precursor of aqualysin I in a host cell.

5. The recombinant vector of claim 4 wherein the gene has a base sequence of from base No. 407 to base No. 1948.

6. An *Escherichia coli* transformed with the recombinant vector of claim 4.

7. An *Escherichia coli* transformed with the recombinant vector of claim 5.

8. A process of producing aqualysin I comprising the steps of:
culturing the *Escherichia coli* of claim 6 in a culture medium;
heat-treating the cultured *Escherichia coli* to 65°-90° C.; and
recovering aqualysin I from the culture medium.

* * * * *